United States Patent [19]

Skuballa et al.

[11] Patent Number: 4,699,920
[45] Date of Patent: Oct. 13, 1987

[54] 9-HALO-2-PROSTAGLANDIN DERIVATIVES, PROCESSES FOR THE PREPARATION THEREOF AND USE THEREOF AS MEDICINAL AGENTS

[75] Inventors: Werner Skuballa; Bernd Raduchel; Helmut Vorbruggen; Walter Elger; Olaf Loge, all of Berlin, Fed. Rep. of Germany

[73] Assignee: Schering Aktiengesellschaft, Berlin and Bergkamen, Fed. Rep. of Germany

[21] Appl. No.: 770,350

[22] PCT Filed: Dec. 21, 1984

[86] PCT No.: PCT/DE84/00280
§ 371 Date: Sep. 17, 1985
§ 102(e) Date: Sep. 17, 1985

[87] PCT Pub. No.: WO85/02841
PCT Pub. Date: Jul. 4, 1985

[30] Foreign Application Priority Data

Dec. 22, 1983 [DE] Fed. Rep. of Germany ....... 3347128

[51] Int. Cl.⁴ .................. C07C 177/00; A61K 31/557
[52] U.S. Cl. .................................... 514/530; 514/573; 514/601; 514/630; 549/415; 560/62; 560/118; 560/121; 562/472; 562/500; 562/503; 564/98; 564/99; 564/217; 564/221
[58] Field of Search ........................ 560/121, 62, 118; 562/503, 500, 472; 549/415; 564/98, 99, 217, 221; 514/530, 573, 601, 630

[56] References Cited

U.S. PATENT DOCUMENTS 4,444,788 4/1984 Skulalla ............................. 560/121
4,562,204 12/1985 Wakatsuka ......................... 560/121

Primary Examiner—Robert Gerstl
Attorney, Agent, or Firm—Millen & White

[57] ABSTRACT

The invention relates to 9-halo-Δ²-prostane derivatives of general Formula I

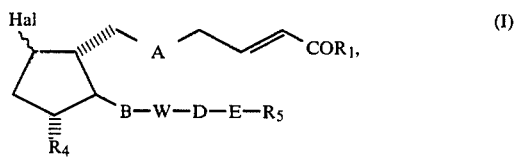

wherein
Hal is a fluorine or chlorine atom in the α- or β-position,
$R_1$ is the residue $OR_2$ with $R_2$ meaning a hydrogen atom, alkyl, cycloalkyl, aryl or a heterocyclic residue; or the residue $NHR_3$ wherein $R_3$ means an acid residue or the residue $R_2$ and
A is a —$CH_2$—$CH_2$— or cis-CH=CH—group,
B is a —$CH_2$—$CH_2$— or trans—CH=CH— or —C≡C—group,
W is a free or functionally modified hydroxymethylene or

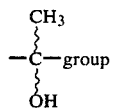

wherein the respective OH-groups can be in the α- or β-position,
D and E jointly mean a direct bond or
D is a straight- or branched-chain alkylene group of 1–10 carbon atoms, which can optionally be substituted by fluorine atoms,
E is an oxygen or sulfur atom, a direct bond, a —C≡C—bond or a —$CR_6$=$CR_7$—group wherein $R_6$ is a hydrogen atom or an alkyl group and $R_7$ is a hydrogen atom, an alkyl group or a halogen atom,
$R_4$ is a free or functionally modified hydroxy group,
$R_5$ is a hydrogen atom, an alkyl group, a halogen-substituted alkyl group, a cycloalkyl group, an optionally substituted aryl group, or a heterocyclic group, and, if $R_2$ means a hydrogen atom, the salts thereof with physiologically compatible bases.

17 Claims, No Drawings

9-HALO-2-PROSTAGLANDIN DERIVATIVES, PROCESSES FOR THE PREPARATION THEREOF AND USE THEREOF AS MEDICINAL AGENTS

The invention relates to novel 9-halo-$\Delta^2$-prostaglandin derivatives, processes for their preparation, as well as their use as medicinal agents.

It is known from the very voluminous state of the art of prostaglandins and their analogs that this class of compounds is suited, based on their biological and pharmacological properties, for the treatment of mammals, including man. The use of these compounds as medicinal agents, however, frequently meets with difficulties. Most of the natural prostaglandins exhibit a period of efficacy which is too short for therapeutic purposes, since they are too rapidly degraded metabolically by various enzymatic processes. All structural modifications serve the purpose of prolonging the duration of efficacy as well as increasing the selectivity of effectiveness.

German Unexamined Laid-Open Applications Nos. 2,950,027 and 3,126,924 disclose prostane derivatives having a chlorine or fluorine atom in the 9-position. It has now been found that a longer period of efficacy, higher selctivity, and improved effectiveness can be attained by the introduction of a double bond into the 2,3-position of the 9-haloprostaglandins.

The invention relates to 9-halo-$\Delta^2$-prostane derivatives of general Formula I

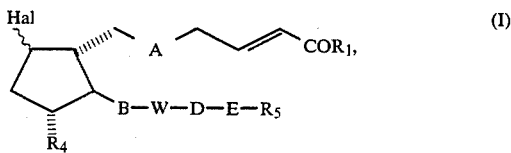

wherein

Hal is a fluorine or chlorine atom in the $\alpha$- or $\beta$-position, $R_1$ is the residue $OR_2$ with $R_2$ meaning a hydrogen atom, alkyl, cycloalkyl, aryl or a heterocyclic residue; or the residue $NHR_3$ wherein $R_3$ means an acid residue or the residue $R_2$ and A is a —$CH_2$—$CH_2$— or cis—CH=CH—group, B is a —$CH_2$—$CH_2$— or trans—CH=CH— or —C≡C—group, W is a free or functionally modified hydroxymethylene

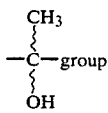

wherein the respective OH-groups can be in the $\alpha$- or $\beta$-position,

D and E jointly mean a direct bond or

D is a straight- or branched-chain alkylene group of 1–10 carbon atoms, which can optionally be substituted by fluorine atoms, E is an oxygen or sulfur atom, a direct bond, a —C≡C—bond or a —$CR_6$=$CR_7$—group wherein $R_6$ is a hydrogen atom or an alkyl group and $R_7$ is a hydrogen atom, an alkyl group or a halogen atom, $R_4$ is a free or functionally modified hydroxy group, $R_5$ is a hydrogen atom, an alkyl group, a halogen-substituted alkyl group, a cycloalkyl group, an optionally substituted aryl group, or a heterocyclic group, and, if $R_2$ means a hydrogen atom, the salts thereof with physiologically compatible bases.

Suitable alkyl groups $R_2$ are linear or branched alkyl groups of 1-10 carbon atoms, such as, for example, methyl, ethyl, propyl, butyl, isobutyl, tert-butyl, pentyl, neopentyl, hexyl, heptyl, decyl. The alkyl groups $R_2$ can optionally be mono- to polysubstituted by halogen atoms, alkoxy groups, optionally substituted aryl or aroyl groups, dialkylamino and trialkylammonium, wherein the single substitution is to be preferred. Examples for substituents are fluorine, chlorine or bromine, phenyl, dimethylamino, diethylamino, methoxy, ethoxy. Preferred alkyl groups $R_2$ that can be cited are those of 1-4 carbon atoms, such as, for example, methyl, ethyl, propyl, dimethylaminopropyl, isobutyl, butyl.

Suitable aryl groups $R_2$ are substituted as well as unsubstituted aryl groups such as, for example, phenyl, 1-naphthyl and 2-naphthyl, each of which can be substituted by 1-3 halogen atoms, a phenyl group, 1-3 alkyl groups of 1-4 carbon atoms each, a chloromethyl, fluoromethyl, trifluoromethyl, carboxy, hydroxy or alkoxy group of 1-4 carbon atoms. Preferred are the substituents in the 3- and 4-positions on the phenyl ring, for example by fluorine, chlorine, alkoxy or trifluoromethyl, or in the 4-position by hydroxy.

The cycloalkyl group $R_2$ can contain 3-10, preferably 5 and 6 carbon atoms in the ring. The rings can be substituted by alkyl groups of 1-4 carbon atoms. Examples that can be cited are cyclopentyl, cyclohexyl, methylcyclohexyl and adamantyl.

Suitable heterocyclic groups $R_2$ are 5- and 6-membered heterocycles containing at least one hetero atom, preferably nitrogen, oxygen or sulfur. Examples that can be cited are 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, 2-tetrazolyl, and others.

Suitable as the acid residue $R_3$ are physiologically compatible acid residues. Preferred acids are organic carboxylic acids and sulfonic acids of 1-15 carbon atoms pertaining to the aliphatic, cycloaliphatic, aromatic, aromatic-aliphatic, and heterocyclic series. These acids can be saturated, unsaturated and/or polybasic and/or can be substituted in the usual way. Examples for substituents that can be mentioned are alkyl, hydroxy, alkoxy, oxo or amino groups, or halogen atoms. The following carboxylic acids are cited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and tri-chloroacetic acids, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy or carboxy groups, nicotinic acid, isonicotinic acid, furan-2-carboxylic acid, cyclopentylpropionic acid. Acyl residues of up to 10 carbon atoms are considered to be especially preferred. Examples for sulfonic acids are methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylam:inosulfonic acid, N,N-dibutylaminosulfonic acid, pyrrolidino-, piperidino-, piperazino-, N-methylpiperazino- and morpholinosulfonic acids.

The hydroxy groups in W and $R_4$ can be functionally modified, for example by etherification or esterification, wherein also the modified hydroxy group in W can be in the α- or β-position.

Suitable ether and acyl residues are those known to a person skilled in the art. Readily cleavable ether residues are preferred, such as, for example, the tetrahydropyranyl, tetrahydrofuranyl, α-ethoxyethyl, trimethylsilyl, dimethylsilyl, tert-butylsilyl and tribenzylsilyl residues. Acyl residues can be the same as cited for $R_3$; examples that can be mentioned are acetyl, propionyl, butyryl and benzoyl.

Suitable alkyl groups $R_5$ are straight- and branched-chain, saturated and unsaturated alkyl residues, preferably saturated ones, of 1–10, especially 1–6 carbon atoms which can, if desired, be substituted by optionally substituted aryl. Examples that can be mentioned are methyl, ethyl, propyl, butyl, isobutyl, tert-butyl, pentyl, hexyl, heptyl, octyl, butenyl, isobutenyl, propenyl, pentenyl, benzyl, m-and p-chlorobenzyl groups.

If the alkyl groups $R_5$ are halogen-substituted, suitable halogens are fluorine, chlorine and bromine.

The cycloalkyl group $R_5$ can contain in the ring 3–10, preferably 3–6 carbon atoms. The rings can be substituted by alkyl groups of 1–4 carbon atoms. Examples that can be cited are cyclopropyl, cyclobutyl, cyclopentyl, cyclohexyl, methylcyclohexyl and adamantyl.

Examples for substituted and unsubstituted aryl groups $R_5$, respectively, are: phenyl, 1-naphthyl and 2-naphthyl, each of which can be substituted by 1–3 halogen atoms, a phenyl group, 1–3 alkyl groups of 1–4 carbon atoms each, a chloromethyl, fluoromethyl, trifluoromethyl, carboxy, alkoxy or hydroxy group. Preferred is the substitution in the 3- and 4-positions on the phenyl ring, for example by fluorine, chlorine, alkoxy or trifluoromethyl, or in the 4-position by hydroxy.

Suitable heterocyclic groups $R_5$ are 5- and 6-membered heterocycles containing at least one hetero atom, preferably nitrogen, oxygen or sulfur. Examples that can be cited are 2-furyl, 2-thienyl, 2-pyridyl, 3-pyridyl, 4-pyridyl, oxazolyl, thiazolyl, pyrimidinyl, pyridazinyl, pyrazinyl, 3-furyl, 3-thienyl, etc.

Suitable alkylene groups D are straight-chain or branched-chain, saturated and unsaturated alkylene residues, preferably saturated ones of 1–10, especially 1–5 carbon atoms, which can optionally be substituted by fluorine atoms. Examples are: methylehe, fluoromethylene, difluoromethylene, ethylene, 1,2-propylene, ethylethylene, trimethylene, tetramethylene, pentamethylene, 1,1-difluoromethylene, 1-fluoroethylene, 1-methyltramehylene, 1-methyltrimethylene, 1-methylenethylene, 1-methylenetetramethylene.

Alkyl groups $R_6$ and $R_7$ that can be used are straight-chain or branched-chain alkyl groups of 1–6 carbon atoms, preferably 1–4 carbon atoms, as recited above for the alkyl groups $R_5$. Halogen for $R_7$ is understood to mean the halogen atoms fluorine, chlorine and bromine, chlorine being preferable.

Suitable for salt formation are inorganic and organic bases as known to those skilled in the art for the formation of physiologically compatible salts. Examples that can be cited are alkali hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

The invention furthermore relates to a process for the preparation of the 9-halo-$\Delta^2$-prostane derivatives of this invention according to general Formula I, characterized in that, in a conventional way, a double bond is introduced in the 2-position into a compound of general formula II

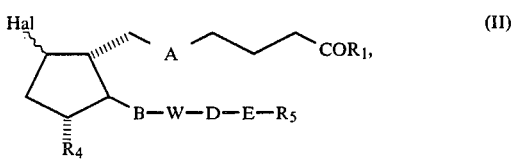

by reaction with a lithium dialkyl amide of general formula III

wherein $R_8$ and $R_9$ mean alkyl group of 1–10 carbon atoms or a cycloalkyl group of 3–6 carbon atoms or a trialkyl-silyl group with alkyl meaning $C_1$-$C_4$-alkyl, subsequently the product is treated with a phenyl compound of general Formula IV

wherein $R_{10}$ represents the residues

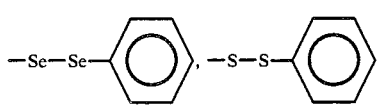

or SeBr, and thereafter, in any desires sequence, an oxidative elimination is performed and/or optionally isomers are separated and/or blocked hydroxy groups are liberated and/or free hydroxy groups are esterified, etherified and/or a free carboxy group is esterified and-/or an esterified carboxy group is saponified or a carboxy group is converted into an amide or, with a phsiologically compatible base, into a salt.

Suitable alkyl groups $R_8$ and $R_9$ are all those groups recited for $R_2$. The same preferred groups are also to apply in this case. Cycloalkyl groups $R_8$ and $R_9$ of 3–6 carbon atoms mean: cyclopropyl, cyclobutyl, cyclopentyl, cyclohexyl.

The reaction of the compounds of general formula II with a lithium amide compound of general formula III, preferably lithium diisopropylamide, takes place conventionally in an inert solvent or solvent mixture, such as, for example, tetrahydrofuran, diethyl ether, hexamethylphosphoramide, dimethoxyethane, etc., preferably tetrahydrofuran. The reaction is conducted at temperatures of between −100° and 0° C., preferably −80° to −50° C. Reaction with diphenyldiselenide, diphenylidisulfide or phenylselenyl bromide takes place at temperatures of between −100° and +30° C., preferably −70° and 0° C. Oxidation of the resultant selenium compound is performed with hydrogen peroxide in an inert solvent or solvent mixture, such as, for example, tetrahydrofuran, ethyl acetate, methyl acetate, methanol, ethanol, isopropanol, etc., at temperatures of between −20° and +60° C., preferably 0°-30° C., the intermediary selenium oxide compound then already being dissociated with the formation of the $\Delta^2$-double bond.

Oxidation of the resultant sulfur compound is suitably effected with sodium periodate in the presence of an alcohol, such as, for example, methanol, ethanol, with the addition of water, at temperatures of between 0° and 60° C., preferably 10°-30° C. Dissociation of the formed sulfoxide into the $\Delta^2$-compound of general Formula I takes place at temperatures of between 30° and 120° C. with addition of a small amount of calcium carbonate in an inert solvent, such as, for example, toluene, xylene, carbon tetrachloride, etc.

Saponification of the prostaglandin esters takes place according to the methods known to persons skilled in the art, such as, for example, with alkaline catalysts or enzymatically, with, for example, lipase, pig's liver esterase, or baker's yeast.

Introduction of the ester group —OR$_2$ for R$_1$, wherein R$_2$ is an alkyl group of 1-10 carbon atoms, takes place according to the methods known to persons skilled in the art. The carboxy compounds are conventionally reacted, for example, with diazo hydrocarbons. Esterification with diazo hydrocarbons takes place, for example, by mixing a solution of the diazo hydrocarbon in an inert solvent, preferably in diethyl ether, with the carboxy compound in the same or in a different inert solvent, e.g. methylene chloride. After the reaction is finished within 1-30 minutes, the solvent is removed and the ester purified as usual. Diazoalkanes are either known or can be prepared according to known methods [Org. Reactions 8 : 389-394 (1954)].

Introduction of the ester group —OR$_2$ for R$_1$, wherein R$_2$ is a substituted or unsubstituted aryl group, takes place according to the methods known to those skilled in the art. For example, the carboxy compounds are reacted with the corresponding aryl hydroxy compounds with dicyclohexylcarbodiimide in the presence of a suitable base, for example pyridine or triethylamine, in an inert solvent, Suitable solvents are methylene chloride, ethylene chloride, chloroform, ethyl acetate, tetrahydrofuran, preferably chloroform. The reaction is carried out at temperatures of between −30° and +50° C., preferably at +10° C.

The prostaglandin derivatives of general Formula I with R$_1$ being a hydroxy group can be converted into salts with suitable amounts of the corresponding inorganic bases under neutralization. For example, the solid inorganic salt is obtained when dissolving the corresponding PG acids in water containing the stoichiometric quantity of the base, after evaporation of the water or after addition of a water-miscible solvent, e.g. alcohol or acetone.

Preparation of the amine salts takes place as usual. For this purpose, the PG acid is dissolved, for example, in a suitable solvent, e.g. ethanol, acetone, diethyl ether or benzene, and at least the stoichiometric amount of the amine is added to this solution. During this process, the salt is ordinarily obtained in the solid form or is isolated as usual after evaporation of the solvent.

The functional modification of the free OH-groups takes place according to methods known to persons skilled in the art. For example, in order to introduce the ether blocking groups, the reaction is conducted with dihydropyran in methylene chloride or chloroform with the use of an acidic condensation agent, for example p-toluenesulfonic acid. The dihydropyran is used in excess, preferably in four to ten times the theoretically needed quantity. The reaction is normally completed at 0-30° C. after 15-30 minutes.

The acyl blocking groups are introduced by conventionally reacting a cmpound of general Formula I with a carboxylic acid derivative, for example an acid chloride, acid anhydride, etc.

The liberation of a functionally modified OH-group to obtain the compounds of Formula I takes place by methods known per se. For example, ether blocking groups are split off in an aqueous solution of an organic acid, such as, for example, acetic acid, propionic acid, etc., or in an aqueous solution of an inorganic acid e.g. hydrochloric acid. In order to improve solubility, a water-miscible, inert organic solvent is suitably added. Suitable organic solvents are, for example, alcohols, such as methanol and ethanol, and ethers, such as dimethoxyethane, dioxane, and tetrahydrofuran. Tetrahydrofuran is preferably employed. The splitting-off step is conducted preferably at temperatures of beteen 20° and 80° C.

The silyl ether blocking groups are split off, for example, with tetrabutylammonium fluoride. Examples for suitable solvent are tetrahydrofuran, diethyl ether, dioxane, methylene chloride, etc. The splitting-off step is preferably conducted at temperatures of between 0° and 80° C.

The acyl groups are saponified, for example, with alkali or alkaline earth carbonates or hydroxides in an alcohol or in the aqueous solution of an alcohol. Suitable alcohols are aliphatic alcohols, e.g. methanol, ethanol, butanol, etc., preferably methanol. Alkali carbonates and hydroxides that can be mentioned are potassium and sodium salts, but the potassium salts are preferred. Suitable alkaline earth carbonates and hydroxides are, for example, calcium carbonate, calcium hydroxide, and barium carbonate. The reaction takes place at −10° to 70° C., preferably at 25° C.

The amide group NHR$_3$ for R$_1$ is introduced according to methods known to those skilled in the art. The carboxylic acids of general Formula I (R$_2$ =H) are first of all converted into the mixed anhydride with the isobutyl ester of chloroformic acid, in the presence of a tertiary amine, e.g. triethylamine. Reaction of the mixed anhydride with the alkali salt of the corresponding amide or with ammonia (R$_3$=H) takes place in an inert solvent or solvent mixture, such as, for example, tetrahydrofuran, dimethoxyethane, dimethylformamide, hexamethylphosphoric triamide, at temperatures of between −30° and +60° C., preferably at 0°-30° C.

Another possibility for introduction of the amide group NHR$_3$ for R$_1$ resides in reacting a 1-carboxylic acid of general Formula I (R$_2$=H) wherein free hydroxy groups are optionally blocked intermediarily, with compounds of general Formula V $$O=C=N-R_3 \qquad V$$

wherein $R_3$ has the meanings given above.

Reaction of the compound of general Formula I ($R_2=H$) with an isocyanate of general Formula V takes place optionally with addition of a tertiary amine, e.g. triethylamine or pyridine. The reaction can take place without solvents or in an inert solvent, preferably acetonitrile, tetrahydrofuran, acetone, dimethylacetamide, methylene chloride, diethyl ether, toluene, at temperatures of between $-80°$ to $100°$ C., preferably at $0-30°$ C.

If the starting compound contains OH-groups in the prostane residue, then these OH-groups are also made to react. If, in the final analysis, end products are desired which contain free hydroxy groups in the prostane residue, then starting compounds are suitably employed wherein these are intermediarily blocked by preferably readily cleavable ether or acyl residues.

The compounds of general Formula II serving as the starting material wherein Hal means a fluorine atom can be prepared, for example, according to DOS No. 3,126,924 by reacting, in a manner known per se, a compound of general Formula VI

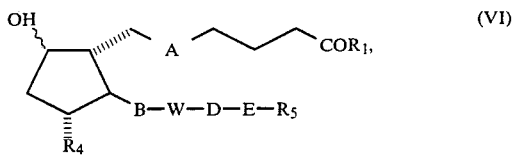

wherein the OH-group can be in the $\alpha$- or $\beta$-position, $R_1$, $R_4$, $R_5$, A, B, W, D and $R_5$ have the meanings given above, and free OH-groups in $R_4$ and W are optionally blocked, with a tetraalkylammonium fluoride by way of an intermediary sulfonic acid ester.

The compounds of general Formula II serving as the starting material wherein Hal means a chlorine atom can be produced, for example, in accordance with DOS No. 2,950,027 by conventionally reacting a compound of general Formula VI (a) by way of an intermediary sulfonic acid ester with a chloride of general Formula VII

wherein $R_{11}$ has the meaning of lithium, sodium, potassium, or tetraalkylammonium with alkyl as a saturated $C_1$-$C_6$-residue, or (b) by chlorinating with the reagent carbon tetrachloride or, respectively, hexachloroethane/triphenyl-phosphine.

As compared with PGE derivatives, the novel 9-halo-$\Delta^2$-prostaglandins are distinguished by greater stability. The novel 9-halo-$\Delta^2$-prostane derivatives of general Formula I are valuable pharmaceuticals since they exhibit, with a similar spectrum of activity, a substantially improved effect (higher specificity) and, above all, substantially longer activity duration than the corresponding natural prostaglandins.

The novel prostaglandin analogs have a strongly uterotropic and luteolytic effect, i.e. for triggering a uterus contraction and/or luteolysis, substantially lesser doses are required than with the corresponding, natural prostaglandins.

Also for triggering abortions; especially upon oral or intravaginal administration, substantially lower amounts of the novel prostaglandin analogs are required, as compared with the natural prostaglandins.

When recording the isotonic uterus contraction on anesthetized rats and on the isolated rat uterus, it is found that the compounds of this invention are substantially more efficacious, and their effects are of a longer duration, than in case of the natural prostaglandins.

The novel prostaglandin derivatives are suitable, after a single enteral or parenteral administration, for inducing menstruation or interrupting pregnancy. They are furthermore suited for synchronizing the sexual cycle in female mammals, such as rabbits, cattle, horses, pigs, etc. Furthermore, the prostaglandin derivatives of this invention are suitable for cervix dilatation as a preparation for diagnostic or therapeutic interventions.

The good tissue specificity of the compounds of this invention exhibiting antifertility effects is demonstrated in studies on other smooth-muscle organs, such as, for example, on the guinea pig ileum or on the isolated rabbit trachea, where a substantially lesser stimulation can be observed than caused by the natural prostaglandins. The compounds of this invention also have bronchospasmolytic effects. Furthermore, they reduce swelling of the nasal mucosa.

The active agents of this invention inhibit gastric acid secretion, they show cytoprotective and ulcer-healing activity and thus counteract the undesirable consequences of nonsteroidal anti-inflammatory compounds (prostaglandin synthesis inhibitors). They furthermore show cytoprotective effects on the liver as well as on the pancreas.

Several of the compounds have antihypertensive effects, exhibit a regulating effect during cardiac arrhythmias and an inhibitory effect on platelet aggregation, with the usage possibilities ensuing therefrom. The novel prostaglandins can also be utilized in combination, for example, with $\beta$-blockers and diuretics.

For medical use, the active agents can be converted into a form suitable for inhalation, for oral, parenteral or local (e.g. vaginal) administration.

For inhalation, aerosol solutions are suitably prepared.

Suitable for oral administration are, for example, tablets, dragees or capsules.

Sterile, injectable, aqueous or oily solutions are utilized for parenteral administration.

Suppositories are suitable and customary, for example, for vaginal administration.

The invention consequently also concerns medicinal agents based on the compounds of general Formula I and the customary auxiliary agents and excipients.

The active agents of this invention are to be utilized, in conjunction with the auxiliary agents known and conventional in galenic pharmacy, for example for the production of preparations for triggering abortion, for cycle control, for initiating labor, or for treatment of hypertonia. For this purpose, but also for the remaining applications, the preparations can contain 0.01–50 mg of the active compound.

The examples set forth below are to describe the invention in greater detail without being limiting.

EXAMPLE 1

(2E,13E)-(9R,11R,15R)-11,15-Dihydroxy-9-fluoro-16-phenoxy-17,18,19,20-tetranor-2,13-prostadienoic Acid Methyl Ester At $-20°$ C., 0.8 ml of a 1.6-molar butyllithium solution in hexane is added dropwise to a solution of 0.28 ml of diisopropylamine in 2.1ml of absolute tetrahydrofuran; the mixture is stirred for 30 minutes under argon at $-20°$ C. At $-70°$ C., a solution of 370 mg of (13E)-

(9R,11R,15R)-11,15-bis(tetrahydropyran-2-yloxy)-9-fluoro-16 phenoxy-17,18,19,20-tetranor-13-prostenoic acid methyl ester in 3.3 ml of absolute tetrahydrofuran is added dropwise to this solution, the mixture is stirred for 30 minutes at −70° C., and thereafter, at −70° C., a solution of 334 mg of diphenyldiselenide in 2.1 ml of absolute tetrahydrofuran is added dropwise thereto. The reaction mixture is agitated for 60 minutes at −40° C., combined with water, acidified with 3% sulfuric acid to pH 6, extracted three times with ether, washed neutral with water, dried over magnesium sulfate, and evaporated under vacuum. The residue is filtered over silica gel with hexane/ethyl acetate (85+15), thus obtaining 285 mg of the 2-phenylselenium compound as a yellowish oil.

For oxidation, a solution of 285 mg of the selenium compound prepared above in 6 ml of methylene chloride and 0.15 ml of pyridine is combined with 0.15 ml of 30% strength hydrogen peroxide solution, and the mixture is stirred for 1.5 hours at 25° C. Subsequently the mixture is diluted with methylene chloride, shaken with 5% sodium bicarbonate solution, washed neutral with water, dried over magnesium sulfate, and evaporated under vacuum. The residue is filtered with toluene/ethyl acetate (9+1) over silica gel, thus obtaining 160 mg of (2E,13E)-(9R,11R,15R)-11,15-bis-(tetrahydropyranyloxy)-9-fluoro-16-phenoxy-17,18,19,20-tetranor-2,13-prostadienoic acid methyl ester.

IR (CHCl$_3$): 2943, 2860, 1716, 1659, 1600, 1578, 1495, 972 cm$^{-1}$.

To split off the blocking groups, 160 mg of the Δ$^2$-compound produced as above is stirred for 16 hours at 25° C. with 8 ml of a mixture of acetic acid, water, THF (65+35+10) and then evaporated under vacuum. The residue is purified by chromatography on silica gel. With methylene chloride/acetone (8+2), 102 mg of the title compound is obtained as a colorless oil.

IR: 3590, 3420 (broad), 2950, 2860, 1712, 1657, 1599, 1588, 1495, 970 cm$^{-1}$.

The starting material for the above title compound is prepared as follows:

1(a)

(13E)-(9R,11R,15R)-11,15-Bis(tetrahydropyran-2-yloxy)-9-fluoro-16-phenoxy-17,18,19,20-tetranor-13-prostenoic Acid Methyl Ester At 0° C., 2.5 mg of p toluenesulfonic acid is added to a solution of 250 mg of (13E)-(9R,11R,15R)-11,15-dihydroxy- 9-fluoro-16-phenoxy-17,18,19,20-tetranor-13-prostenoic acid methyl ester and 160 mg of dihydropyran in 16 ml of mthylene chloride, and the mixture is agitated for 30 minutes at 0° C. Subsequently the mixture is diluted with ether, shaken with 5% sodium bicarbonate solution and water, dried over magnesium sulfate, and evaporated under vacuum. The residue is chromatographed with hexane/ethyl acetate (9+1) on silica gel, thus obtaining 330 mg of the title compound as a colorless oil.

IR: 2945, 2860, 1732, 1599, 1688, 1495, 970 cm$^{-1}$.

EXAMPLE 2

(2E,13E)-(9R,11R,15R)-11,15-Dihydroxy-9-fluoro-16-phenoxy-17,18,19,20-tetranor-2,13-prostadienoic Acid 102 mg of the methyl ester prepared according to Example 1 is stirred for 5 hours with 6 ml of a solution of potassium hydroxide in ethanol and water (preparation: 2 g of potassium hydroxide is dissolved in 75 ml of ethanol and 25 ml of water). Then the mixture is acidified to pH 4 with 10% citric acid solution, extracted three times with methylene chloride, the organic extract is washed once with brine, dried over magnesium sulfate, and evaporated under vacuum. Chromatography of the residue on silica gel with methylene chloride/isopropanol (92+8) as the eluting agent yields 84 mg of the title compound as a colorless oil.

IR: 3600, 3400 (broad), 2930, 2859, 1696, 1652, 1599, 1588, 1494, 970 cm$^{-1}$.

EXAMPLE 3

(2E,13E)-(9S,11R,15R)-11,15-Dihydroxy-9-fluoro-16-phenoxy-17,18,19,20-tetranor-2,13-prostadienoic Acid Methyl Ester Analogously to Example 1, 400 mg of (13E)-(9S,11R,15R)-11,15-bis(tetrahydropyran-2-yloxy)-9-fluoro-16-phenoxy-17,18,19,20-tetranor-13-prostenoic acid methyl ester yields 180 g of (2E,13E)-(9S,11R,15R)-11,15-bis-(tetrahydropyranyloxy)-9-fluoro-16-phenoxy-17,18,19,20-tetranor-2,13-prostadienoic acid methyl ester.

After the blocking groups have been split off according to Example 1, 120 mg of the title compound is obtained as a colorless oil.

IR: 3600, 3410 (broad), 2950, 2860, 1711, 1657, 1600, 1589, 970 cm$^{-1}$.

The starting material for the above title compound is produced as follows:

3(a)

(13E)-(9S,11R,15R)-11,15-Bis(tetrahydropyran-2-yloxy)-9-fluoro-16-phenoxy-17,18,19,20-tetranor-13-prostenoic Acid Methyl Ester In analogy to Example 1(a), 380 mg of (13E)-(9S,11R,15R)-11,15-Dihydroxy-9-fluoro-16-phenoxy-17,18,19,20-tetranor-13-prostenoic acid methyl ester yields 450 mg of the title compound as a colorless oil.

IR: 2946, 2860, 1731, 1600, 1589, 971 cm$^{-1}$.

EXAMPLE 4

(2E,13E)-(9S,11R,15R)-11,15-Dihydroxy-9-fluoro-16-phenoxy-17,18,19,20-tetranor-2,13-prostadienoic Acid In analogy to Example 2, 140 mg of the methyl ester prepared according to Example 3 yields 120 mg of the title compound as a colorless oil.

IR: 3610, 3410 (broad), 2931, 2860, 1697, 1652, 1600, 1589, 971 cm$^{-1}$.

EXAMPLE 5

(2E,13E)-(9R,11R,15R)-11,15-Dihydroxy-16,16-dimethyl-9-fluoro-2,13-prostadienoic Acid Methyl Ester Analogously to Example 1, 250 mg of (13E)-(9R,11R,15)-16,16-dimethyl-11,15-bis(tetrahydropyran-2-yloxy)-9-fluoro-13-prostenoic acid methyl ester yields 203 mg of (2E,13E)-(9R,11R,15R)-16,16-dimethyl-11,15-bis(tetrahydropyran-2-yloxy)-9-fluoro-2,13-prostadienoic acid methyl ester.

After splitting off the blocking groups according to Example 1, 135 mg of the title compound is obtained as a colorless oil.

IR: 3600, 3400, 2960, 2936, 2875, 1718, 1656, 973 cm$^{-1}$.

The starting material for the above title compound is prepared as follows:

5(a)

(13E)-(9R, 11R,15R)-16,16-Dimethyl-11,15-bis(tetrahydropyran-2-yloxy)-9-fluoro-13-prostenoic Acid Methyl Ester Analogously to Example 1(a), 300 mg of (13E)-(9R, 11R,15R)-11,15-dihydroxy-16,16-dimethyl-9-fluoro-13-prostenoic acid methyl ester produces 360 mg of the title compound as a colorless oil.

IR: 2942, 2858, 1736, 973 cm$^{-1}$.

EXAMPLE 6

(2E,13E)-(9R, 11R,15R)-11,15-Dihydroxy-16,16-dimethyl-9-fluoro-2,13-prostadienoic Acid In analogy to Example 2, 100 mg of the methyl ester prepared according to Example 5 yields 81 mg of the title compound as a colorless oil.

IR: 3605, 3410, 2960, 2932, 2876, 1699, 1650, 972 cm$^{-1}$.

EXAMPLES 7

(2E,13E)-(9R, 11R,15S,16RS)-11,15-Dihydroxy-9-fluoro-16-methyl-2,13-prostadienoic Acid Methyl Ester Analogously to Example 1, 300 mg of (13E)-(9R, 11R,15S,16RS)-11,15-bis(tetrahydropyran-2-yloxy)-9-fluoro-16-methyl-13-prostenoic acid methyl ester yields 235 mg of (2E,13E)-(9R, 11R,15S,16RS)-11,15-bis(tetrahydropyran-2-yloxy)-9-fluoro-16-methyl-2,13-prostadienoic acid methyl ester.

After splitting off the blocking groups as described in Example 1, 145 mg of the title compound is obtained as a colorless oil.

IR: 3600, 3410, 2960, 2935, 2872, 1715, 1655, 972 cm$^{-1}$.

The starting material for the above title compound is prepared as follows:

7(a)

(13E)-(9R, 11R,15R,16RS)-11,15-Bis(tetrahydropyran-2-yloxy)-9-fluoro-16-methyl-13-prostexoic Acid Methyl Ester In analogy to Example 1(a), 310 mg of (13E)-(9R, 11R,15S,16RS)-11,15-dihydroxy-9-fluoro-16-methyl-13prostenoic acid methyl ester yields 359 mg of the title compound as a colorless oil.

IR: 2960, 2935, 2872, 1738, 976 cm$^{-1}$.

EXAMPLE 8

(2E,13E)-(9R, 11R,15S,16RS)-11,15-Dihydroxy-9-fluoro-16-methyl-2,13-prostadienoic Acid In analogy to Example 2, 100 mg of the methyl ester prepared according to Example 7 yields 80 mg of the title compound as a colorless oil.

IR: 3605, 3400, 2960, 2935, 2875, 1700, 1652, 973 cm$^{-1}$.

EXAMPLE 9

(2E,13E)-[9R, 11R,15S,16RS)-11,15-Dihydroxy-16,19-dimethyl-9-fluoro-2,13,18-prostatrienoic Acid Methyl Ester In analogy to Example 1, 300 mg of (13E)-(9R, 11R,15S,16RS)-11,15-bis(tetrahydropyran-2-yloxy)-16,19-dimethyl-9-fluoro-13,18-prostadienoic acid methyl ester yields 230 mg of (2E,13E)-(9R, 11R,15S,16RS)-11,15-bis(tetrahydropyran-2-yloxy)-16,19-dimethyl-9-fluoro-2,13,18-prostatrienoic acid methyl ester.

After the blocking groups have been split off as set forth in Example 1, 132 mg of the title compound is obtained as a colorless oil.

IR: 3600, 3410, 2960, 2932, 2878, 1715, 1655, 974 cm$^{-1}$.

The starting material for the above title compound is produced as set out below:

9(a)

(13E)-(9R, 11R,15S,16RS)-11,15-Bis(tetrahydropyran-2-yloxy)-16,19-dimethyl-9-fluoro-13,18-prostadienoic Acid Methyl Ester Analogously to Example 1(a), 250 mg of (13E)-(9R, 11R,15S,16RS)-11,15-dihydroxy-16,19-dimethyl-9-fluoro-13,18-prostadienoic acid methyl ester produces 355 mg of the title compound as a colorless oil.

IR: 2962, 2855, 1736, 974 cm$^{-1}$.

EXAMPLE 10

(2E,13E)-(9R, 11R,15S,16RS)-11,15-Dihydroxy-16,19-dimethyl-9-fluoro-2,13,18-prostatrienoic Acid Analogously to Example 2, 130 mg of the methyl ester prepared according to Example 9 yields 105 mg of the title compound as a colorless oil.

IR: 3605, 3405, 2959, 2935, 2858, 1700, 1649, 974 cm$^{-1}$.

EXAMPLE 11

(2E,13E)-(9R, 11R,15RS)-11,15-Dihydroxy-9-fluoro-15-methyl-2,13-prostadienoic Acid Methyl Ester Analogously to Example 1, 200 mg of (13E)-(9R, 11R,15RS)-11,15-bis(tetrahydropyran-2 yloxy)-9-fluoro-15-ethyl-13-prostenoic acid methyl ester produces 150 mg of (2E,13E)-(9R, 11R,15RS)-11,15-bis(tetrahydropyran-2-yloxy)-fluoro-15-methyl-2,13-prostadienoic acid methyl ester.

After the blocking groups have been split off according to Example 1, 80 mg of the title compound is obtained as a colorless oil.

IR: 3600, 3410 (broad), 2960, 2881, 1715, 1658, 974 cm$^{-1}$.

The starting material for the above title compound is produced as set forth below:

11(a) (13E)-(9R, 11R,15RS)-11,15-Bis(tetrahydropyran-2-yloxy)-9-fluoro 15-methyl-13-prostenoic Acid Methyl Ester A solution of 400 mg of (5Z,13E)-(9R, 11R,15RS)-11,15-bis(tetrahydropyran-2 -yloxy)-9-fluoro-15-methyl-5,13-prostadienoic acid methyl ester in 50 ml of ethyl acetate is shaken with 40 mg of palladium/10% strength on carbon under a hydrogen atmosphere at 0° C. After absorption of 1 equivalent of hydrogen, the product is filtered off from the catalyst and evaporated under vacuum. The residue is absorbed on silica gel. With hexane/5-20% diethyl ether, 300 mg of the title compound is eluted as a colorless oil.

IR: 2958, 2850, 1738, 976 cm$^{-1}$.

EXAMPLE 12

(2E,13E)-(9R, 11R,15RS)-11,15-Dihydroxy-9-fluoro-15-methyl-2,13-prostadienoic Acid Analogously to Example 2, 70 mg of the methyl ester prepared according to Example 11 yields 55 mg of the title compound as a colorless oil.

IR: 3600, 3410 (broad), 2960, 2855, 1701, 1652, 974 cm$^{-1}$.

EXAMPLE 13

(2E,13E)-(9R, 11R,15S)-11,15-Dihydroxy-9-fluoro-2,13-prostadienoic Acid methyl Ester In analogy to Example 1, 300 mg of (13E)-(9R, 11R,15S)-11,15-bis(tetrahydropyran-2-yloxy)-9-fluoro-13-prostenoic acid methyl ester yields 235 mg of (2E,13E)-(9R, 11R,15S)-11,15-bis(tetrahydropyran-2-yloxy)-9-fluoro-2,13-prostadienoic acid methyl ester.

After splitting off the blocking groups as set forth in Example 1, 140 mg of the title compound is obtained as a colorless oil.

IR: 3600, 3410, 2958, 2862, 1718, 1656, 974 cm$^{-1}$.

The starting material for the above title compound is prepared as follows:

13(a) (13E)-(9R, 11R,15S)-11,15-Bis(tetrahydropyran-2-yloxy)-9-fluoro-13-prostenoic Acid Methyl Ester In analogy to Example 11(a), 500 mg of (5Z,13E)-(9R, 11R,15S)-11,15-bis(tetrahydropyran-2-yloxy)-9-fluro-5,13-prostadienoic acid methyl ester is hydrogenated, thus obtaining 405 mg of the title compound as a colorless oil.

IR: 2960, 1738, 976 cm$^{-1}$.

EXAMPLE 14

(2E,13E)-(9R, 11R,15S)-11,15-Dihydroxy-9-fluoro-2,13-prostadienoic Acid

Analogously to Example 2, 100 mg of the methyl ester produced as set forth in Example 13 yields 86 mg of the title compound as a colorless oil.

IR: 3600, 3410 (broad), 2957, 1698, 1651 976 cm$^{-1}$.

EXAMPLE 15

(2E,13E)-(9R, 11R,15R)-9-Chloro-11,15-dihydroxy-16-phenoxy-17,18,19,20-tetranor-2,13-prostadienoic Acid Methyl Ester A solution is prepared from 0.36 ml of diisopropylamine and 3 ml of absolute tetrahydrofuran and combined at −20° C. with 1.04 ml of a 1.6-molar buty llithium solution in hexane; the mixture is agitated for 30 minutes at −20° C. under argon. At −70° C., a solution of 500 mg of (13E)-(9R, 11R,15R)-11,15-bis(tetrahydropyran-2-yloxy)-9-chloro-16-phenoxy-17,18,19,20-tetranor-13-prostenoic acid methyl ester in 5 ml of absolute tetrahydrofuran is added dropwise to this solution; the mixture is stirred for 30 minutes at −70° C. and then a solution of 434 mg of diphenyldiselenide in 3 ml of absolute tetrahydrofuran is added dropwise. After one hour at −40° C., the mixture is diluted with water, adjusted to pH 6 with 3% sulfuric acid, extracted several times with ether, the extract is shaken with brine, dried over magnesium sulfate, and evaporated under vacuum.

The crude product (371 g of a ye llow oil) is dissolved in 8 ml of dichloromethane and 0.2 ml of pyridine, combined with 0.2 ml of 30% strength hydrogen peroxide solution, and agitated for 1.5 hours at room temperature. Then the mixture is diluted with dichloromethane, shaken with sodium bicarbonate solution and brine, dried over magnesium sulfate, and evaporated under vacuum. For purification, the product is adsorbed on silica gel and eluted with hexane/ethyl acetate (85:15), thus obtaining 205 mg of (2E,13E)-(9R, 11R,15R)-11,15-bis(tetrahydropyran-2-yloxy)-9-chloro-16-phenoxy-17,18,19,20-tetranor-2,13-prostadienoic acid methyl ester as an oil.

IR: 2958, 2849, 1718, 1658, 1600, 1580, 874 cm$^{-1}$.

In order to split off the blocking groups, 205 mg of the Δ$^2$-compound, prepared as described above, is stirred overnight at room temperature with 10 ml of acetic acid/ water/tetrahydrofuran (65/35/15) and then evaporated under vacuum. The product is purified on silica gel with dichloromethane/acetone (8:2), thus obtaining 128 mg of the title compound as a colorless oil.

IR: 3600, 3410 (broad), 2955, 2860, 1710, 1655, 1600, 1585, 972 cm$^{-1}$.

The starting material for the above title compound is produced as described below:

15(a)
(13E)-(9R, 11R,15R)-11,15-Bis(tetrahydropyran-2-yloxy)-9-chloro-16-phenoxy-17,18,19,20-tetranor-13-prostenoic Acid Methyl Ester At 0° C., 290 mg of dihydropyran and 5 mg of p-toluenesulfonic acid are added to a solution of 450 mg of (13E)-(9R, 11R,15R)-9-chloro-11,15-dihydroxy-16-phenoxy-17,18,19,20-tetranor-13-prostenoic acid methyl ester in 20 ml of dichloromethane. After 30 minutes, the mixture is diluted with dichloromethane, shaken with sodium bicarbonate solution and brine, dried over magnesium sulfate, and evaporated under vacuum. The residue is chromatographed with hexane/ethyl acetate (9:1) on silica gel, thus obtaining 570 mg of the title compound as a colorless oil.

IR: 2952, 2862, 1738, 1600, 1585, 972 cm$^{-1}$.

Example 16

(2E,13E)-(9R, 11R,15R)-9-Chloro-11,15-dihydroxy-16-phenoxy-17,18,19,20-tetranor-2,13-prostadienoic Acid In analogy to Example 2, 90 mg of the methyl ester prepared as set forth in Example 15 yields 75 mg of the title compound as a colorless oil.

IR: 3600, 3405 (broad), 2958, 2932, 2852, 1698, 1650, 1600, 1588, 972 cm$^{-1}$.

EXAMPLE 17 (2E,13E)-(9S, 11R,15R)-9-Chloro-11,15-dihydroxy-16-phenoxy-17,18,19,20-tetranor-2,13-prostadienoic Acid Methyl Ester Analogously to Example 15, 350 mg of (13E)-(9S, 11R,15R)-11,15-bis(tetrahydropyran-2-yloxy)-9-chloro-16-phenoxy-17,18,19,20-tetranor-13-prostenoic acid methyl ester yields 280 mg of (2E,13E)-(9S, 11R,15R)-11,15-bis(tetrahydropyran-2-yloxy)-9-chloro-16-phenoxy-17,18,19,20-tetranor-2,13-prostadienoic acid methyl ester.

After splitting off the blocking groups as set forth in Example 15, 160 mg of the title compound is obtained as a colorless oil.

IR: 3600, 3405 (broad), 2958, 2932, 2860, 1712, 1658, 1600, 1588, 976 cm$^{-1}$.

The starting material is produced as follows:

17(a)
(13E)-(9S, 11R,15R)-11,15-Bis(tetrahydropyran-2-yloxy)-9-chloro-16-phenoxy-17,18,19,20-tetranor-13-prostenoic Acid Methyl Ester In analogy to Example 15(a), 350 mg of (13E)-(9S, 11R,15R)-9-chloro-11,15-dihydroxy-16-phenoxy 17,18,19,20-tetranor-13-prostenoic acid methyl ester produces 430 mg of the title compound as a colorless oil.

IR: 2955, 2860, 1738, 1600, 1588, 974 cm$^{-1}$.

EXAMPLE 18

(2E,13E)-(9S, 11R,15R)-9-Chloro-11,15-dihydroxy-16-phenoxy-17,18,19,20-tetranor-2,13- , prostadienoic Acid In analogy to Example 2, 150 mg of the methyl ester prepared according to Example 17 yields 130 mg of the title compound as a colorless oil.

IR: 3605, 3410 (broad), 2952, 2930, 2862, 1700, 1651, 1600, 1585, 874 cm$^{-1}$.

EXAMPLE 19

(2E,13E)-(9R, 11R,15R)-9-Chloro-11,15-dihydroxy-16,16-dimethyl-2,13-prostadienoic Acid Methyl Ester Analogously to Example 15, 250 mg of (13E)-(9R, 11R,15R)-11,15-bis(tetrahydropyran-2-yloxy)-9-chloro-16,16-dimethyl-13-prostenoic acid methyl ester produces 180 mg of (2E,13E)-(9R, 11R,15R)-11,15-bis(tetrahydropyran-2-yloxy)-9-chloro-16,16-dimethyl-2,13-prostodienoic acid methyl ester.

After splitting off the blocking groups according to Example 15, 85 mg of the title compound is obtained as a colorless oil.

IR: 3600, 3405 (broad), 2960, 2935, 2872, 1715, 1658, 976 cm$^{-1}$.

The starting material is prepared as set out below:

19(a)

(13E)-(9R, 11R,15R)-11,15-Bis(tetrahydropyran-2-yloxy)-9-chloro-16,16-dimethyl-13-prostenoic Acid Methyl Ester In analogy to Example 15(a), 220 mg of (13E)-(9R, 11R,15R)-9-chloro-11,15-dihydroxy-16,16-dimethyl-13-prostenoic acid methyl ester yields 280 mg of the title compound as a colorless oil.

IR: 2955, 2870, 1738, 974 cm$^{-1}$.

EXAMPLE 20

(2E,13E)-(9R, 11R,15R)-9-Chloro-11,15-dihydroxy-16,16-dimethyl-2,13-prostadienoic Acid In analogy to Example 2, 80 mg of the methyl ester prepared according to Example 19 yields 65 mg of the title compound as a colorless oil.

IR: 3605, 3420 (broad), 2960, 2872, 1701, 1652, 974 cm$^{-1}$.

EXAMPLE 21

(2E,13E)-(9R, 11R,15S,16RS)-9-Chloro-11,15-dihydroxy-16-methyl-2,13-prostadienoic Acid Methyl Ester Analogously to Example 15, 200 mg of (13E)-(9R, 11R,15S,16RS)-11,15-bis(tetrahydropyran-2-yloxy)-9-chloro-16-methyl-13-prostenoic acid methyl ester yields 160 mg of (2E,13E)-(9R, 11R,15S,16RS)-11,15-bis(tetrahydropyran-2-yloxy)-9-chloro-16-methyl-2,13-prostadienoic acid methyl ester.

After splitting off the blocking groups according to Example 15, 80 mg of the title compound is obtained as a colorless oil.

IR: 3600, 3405 (broad), 2952, 2934, 2870, 1716, 1658, 974 cm$^{-1}$.

The starting material is produced as follows:

21(a)

(13E)-(9R, 11R,15S,16RS)-11,15-Bis(tetrahydropyran-2-yloxy)-9-chloro-16-methyl-13-prostenoic Acid Methyl Ester In analogy to Example 15(a), 200 mg of (13E)-(9R, 11R,15S,16RS)-9-chloro-11,15-dihydroxy-16-methyl-13-prostenoic acid methyl ester produces 255 mg of the title compound as a colorless oil.

IR: 2958, 2862, 1735, 976 cm$^{-1}$.

EXAMPLE 22

(2E,13E)-(9R, 11R,15S,16RS)-9-Chloro-11,15-dihydroxy-16-methyl-2,13-prostadienoic Acid In analogy to Example 2, 70 mg of the methyl ester prepared as set forth in Example 21 yields 50 mg of the title compound as a colorless oil.

IR: 3600, 3410 (broad), 2958, 2935, 2872, 1698, 1651, 974 cm$^{-1}$.

EXAMPLE 23

(2E,13E)-(9R, 11R,15RS)-9-Chloro-11,15-dihydroxy-15-methyl-2,13-prostadienoic Acid Methyl Ester Analogously to Example 15, 400 mg of (13E)-(9R, 11R,15RS)-11,15-bis(tetrahydropyran-2-yloxy)-9-chloro-15 15-methyl-13-prostenoic acid methyl ester yields 320 mg of (2E,13E)-(9R, 11R,15RS)-11,15-bis(tetrahydropyran-2-yloxy)-9-chloro-15-methyl-2,13-prostadienoic acid methyl ester.

After splitting off the blocking groups according to Example 15, 180 mg of the title compound is obtained as a colorless oil.

IR: 3600, 3400, 2955, 2870, 1718, 1657, 976 cm$^{-1}$.

The starting material is produced as set out below:

23(a)

(13E)-(9R, 11R,15RS)-11,15-Bis(tetrahydropyran-2-yloxy)-9-chloro-15-methyl-13-prostenoic Acid Methyl Ester Analogously to Example 11(a), 600 mg of (5Z,13E)-(9R, 11R,15RS)-11,15-bis(tetrahydropyran-2-yloxy)-9-chloro-15-methyl-5,13-prostadienoic acid methyl ester is selectively hydrogenated, thus obtaining 480 mg of the title compound as a colorless oil.

IR: 2960, 2872, 1735, 974 cm$^{-1}$.

EXAMPLE 24

(2E,13E)-(9R, 11R,15RS)-9-Chloro-11,15-dihydroxy-15-methyl-2,13-prostadienoic Acid In analogy to Example 2, 150 mg of the methyl ester prepared according to Example 23 yields 125 mg of the title compound as a colorless oil.

IR: 3605, 3410 (broad), 2958, 2930, 2875, 1700, 1652, 976 cm$^{-1}$.

EXAMPLE 25

(2E,13E)-(9R, 11R,15S)-9-Chloro-11,15-dihydroxy-2,13-prostadienoic Acid Methyl Ester Analogously to Example 15, 250 mg of (13E)-(9R, 11R,15S)-11,15-bis(tetrahydropyran-2-yloxy)-9-chloro-2,13-prostenoic acid methyl ester yields 205 mg of (2E,13E-(9 R, 11R,15S)-11,15-bis(tetrahydropyran-2-yloxy)-9-chloro-2,13-prostadienoic acid methyl ester.

After the blocking groups have been split off as set forth in Example 15, 125 mg of the title compound is obtained as a colorless oil.

IR: 3605, 3410 (broad), 2959, 2938, 2870, 1715, 1655, 974 cm$^{-1}$.

The starting material is prepared as described below:

25(a)

(13E)-(9R, 11R,15S)-11,15-Bis(tetrahydropyran-2-yloxy)-9-chloro-13-prostenoic Acid Methyl Ester Analogously to Example 11(a), 415 mg of (5Z,13E)-(9R, 11R,15S)-11,15-bis(tetrahydropyran-2-yloxy)-9-chloro-5, 13-prostadienoic acid methyl ester is selectively hydrogenated, yielding 337 mg of the title compound as a colorless oil.

IR: 2953, 2868, 1738, 976 cm$^{-1}$.

EXAMPLE 26

(2E,13E)-(9R, 11R,15S)-9-Chloro-11,15-dihydroxy-2,13-prostadienoic Acid

Analogously to Example 2, 97 mg of the methyl ester prepared according to Example 25 yields 78 mg of the title compound as a colorless oil.

IR: 3605, 3410 (broad), 2958, 2935, 2873, 1700, 1651, 975 cm$^{-1}$.

EXAMPLE 27

(2E,5Z,13E)-(9R, 11R,15R)-9-Chloro-11,15-dihydroxy-16,16-dimethyl-2,5,13-prostatrienoic Acid Methyl Ester In analogy to Example 15, 285 mg of (5Z,13E)-(9R, 11R,15R)-11,15-bis(tetrahydropyran-2-yloxy)-9 16,16-dimethyl-5,13-prostadienoic acid methyl ester yields 222 mg of (2E,5Z,13E)-(9R, 11R,15R)-11,15-bis(tetrahydropyran-2-yloxy)-9-chloro-16,16-2,5,13-prostatrienoic acid methyl ester.

After splitting off the blocking groups as set forth in Example 15, 125 mg of the title compound is obtained as a colorless oil.

IR: 3600, 3405, 2958, 2932, 2873, 1715, 1657, 975 cm$^{-1}$.

The starting material is prepared as follows:

27(a)

(5Z,13E)-(9R, 11R,15R)-11,15-Bis(tetrahydropyran-2-yloxy)-9-chloro-16,16-dimethyl-5,13-prostadienoic Acid Methyl Ester In analogy to Example 15(a), 240 mg of (5Z,13E)-(9R, 11R,15R)-9-chloro-11,15-dihydroxy-16,16-dimethyl-5,13-prostadienoic acid methyl ester yields 328 mg of the title compound as a colorless oil.

IR: 2957, 2862, 1738, 974 cm$^{-1}$.

EXAMPLE 28

(2E,5Z,13E)-(9R, 11R,15R)-9-Chloro-11,15-dihydroxy-16,16-dimethyl-2,5,13-prostatrienoic Acid 1.10 g of lipase (EC 3.1.1.3, 20 units/mg) is dissolved in 200 ml of water, and a gentle argon stream is continuously passed through the solution. A pH of 7.0 is set by adding 0.01N sodium hydroxide solution. Then a solution of 125 mg of the methyl ester prepared according to Example 27 in 0.5 ml of ethanol is added dropwise to the reaction mixture and the latter is stirred for 24 hours at room temperature, maintaining the pH of the solution at 7.2 by adding 0.01N sodium hydroxide solution. For isolating purposes, a pH of 4 is set with citric acid and the mixture is extracted repeatedly with ethyl acetate. The combined extracts are shaken with brine, dried over magnesium sulfate, and evaporated under vacuum. The residue is purified by chromatography on silica gel with hexane/ethyl acetate, yielding, as the less polar fraction, 25 mg of unreacted starting material and, as the more polar fraction, 76 mg of the title compound as a colorless oil.

IR: 3605, 3405 (broad), 2957, 2932, 2875, 1701, 1651, 976 cm$^{-1}$.

EXAMPLE 29

(2E,5Z,13E)-(9R, 11R,15R)-11,15-Dihydroxy-16,16-dimethyl-9-fluoro-2,5,13-prostatrienoic Acid Methyl Ester In analogy to Example 15, 275 mg of (5Z,13E)-(9R, 11R,15R)-11,15-bis(tetrahydropyran-2-yloxy)-16,16-dimethyl-9-fluoro-5,13-prostadienoic acid methyl ester yields 219 mg of (2E,5Z,13E)-(9R, 11R,15R)-11,15-bis(tetrahydropyran-2-yloxy)-16,16-dimethyl-9-fluoro-2,5,13-prostatrienoic acid methyl ester.

After splitting off the blocking groups according to Example 15, 130 mg of the title compound is obtained as a colorless oil.

IR: 3605, 3400 (broad), 2961, 2935, 2875, 1716, 1658, 976 cm$^{-1}$.

The starting material is obtained as follows:

29(a)

(5Z,13E)-(9R, 11R,15R)-11,15-Bis(tetrahydropyran-2-yloxy)-16,16-dimethyl-9-fluoro-5,13-prostadienoic Acid Methyl Ester Analogously to Example 15(a), 210 mg of (5Z,13E)-(9R, 11R,15R)-11,15-dihydroxy-16,16-dimethyl-9-fluoro-5,13-prostadienoic acid methyl ester yields 280 mg of the title compound as a colorless oil.

IR: 2957, 2860, 1738, 976 cm$^{-1}$.

EXAMPLE 30

(2E,5Z,13E)-[9R, 11R,15R)-11,15-Dihydroxy-16,16-dimethyl-9-fluoro-2,5,13-prostatrieno Acid In analogy to Example 28, 100 mg of the methyl ester prepared according to Example 29 yields, by reaction with lipase, 60 mg of the title compound as a colorless oil.

IR: 3605, 3410 (broad), 2955, 2932, 2872, 1698, 1650, 975 cm$^{-1}$.

EXAMPLE 31

(2E,13E)-(9R, 11R,15R)-11,15-Dihydroxy-9-fluoro-16-phenoxy-17,18,19,20-tetranor-2,13-prostadienoic Acid Methylsulfonamide A solution of 194 mg of (2E,13E)-(9R, 11R,15R)-11,15-dihydroxy-9-fluoro-16-phenoxy-17,18,19,20-tetranor-2, 13-prostadienoic acid in 3 ml of dimethylformamide is combined with 53 mg of triethylamine and 75 mg of isobutyl chloroformate, and the mixture is stirred for 30 minutes at 0° C. Then the mixture is combined with 236 mg of methylsulfonamide sodium salt and 0.5 ml of hexamethylphosphoric triamide and stirred overnight at 25° C. For working-up purposes, the mixture is diluted with water, acidified with dilute sulfuric acid to pH 3, and repeatedly extracted with ethyl acetate. The combined extracts are washed with brine, dried over magnesium sulfate, and evaporated under vacuum. The residue is chromatographed on silica gel with hexane/ethyl acetate, thus obtaining 135 mg of the title compound as a colorless oil.

IR: 3600, 3410, 2956, 2850, 1701, 1658, 1600, 1589, 976 cm$^{-1}$.

EXAMPLE 32

(2E,13E)-(9R, 11R,15R)-9-Chloro-11,15-dihydroxy-16,16-dimethyl-2,13-prostadienoic Acid N-Acetylamide 250 mg of (2E,13E)-(9R, 11R,15R)-11,15-bis(tetrahydropyran-2-yloxy)-9-chloro-16,16-dimethyl-2,13-prostadienoic acid methyl ester is combined with a solution of 60 mg of potassium hydroxide in 2.5 ml of ethanol and 0.75 ml of water and agitated for 2 hours at room temperature. The mixture is then concentrated under vacuum, diluted with 100 ml of citrate buffer (pH 4), extracted repeatedly with dichloromethane, dried over magnesium sulfate, and evaporated under vacuum. For drying purposes, the residue is dissolved respectively three times in 1 ml of benzene and the solution evaporated under vacuum. The thus-obtained prostaglandin acid is dissolved in 2 ml of acetonitrile and combined in succession, at 0° C., with 125 mg of triethylamine and 200 mg of acetyl isocyanate. The mixture is allowed to stand for 2 hours at 20° C., evaporated under vacuum, combined with water, acidified to pH 5 with citric acid, and extracted with ether. The extract is washed with brine, dried over magnesium sulfate, and evaporated under vacuum. In order to split off the blocking groups, the residue is stirred for 4 hours at 40° C. with 5 ml of a mixture of acetic acid/water/tetrahydrofuran (65/35/10), evaporated under vacuum the residue is absorbed on 50 g of silica gel. By elution with hexane/ethyl acetate, 115 mg of the title compound is obtained as a light-yellow oil.

IR: 3600, 3410, 2956, 2868, 1702, 1658, 1505, 978 cm$^{-1}$.

EXAMPLE 33

(2E,13E)-(9R, 11R,15R)-11,15-Dihydroxy-9-fluoro-16-phenoxy-17,18,19,20-tetranor-2,13-prostadienoic Acid Tris(hydroxymethyl)aminomethane Salt Under agitation, a solution of 75 mg of tris(hydroxymethyl)aminomethane in 0.25 ml of water is added to a solution of 233 mg of (2E,13E)-(9R, 11R,15R)-11,15-dihydroxy-9-fluoro-16-phenoxy-17,18,19,20-tetranor-2,13-prostadienoic acid in 35 ml of acetonitrile, and the mixture is allowed to cool down to room temperature within 5 hours under agitation. The thus-precipitated powder is suctioned off, obtaining, after drying under vacuum, 222 mg of the title compound.

What is claimed is:

1. A 9-halo-$\Delta^2$-prostane of the formula

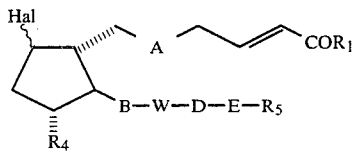

wherein

Hal is a fluorine or chlorine atom in the alpha- or beta-position, $R_1$ is the residue $OR_2$ or $NHR_3$, $R_2$ is (a) a hydrogen atom, (b) $C_{1-10}$-alkyl, (c) $C_{1-10}$-alkyl substituted by halogen, alkoxy, $C_{6-10}$ aryl, $C_{6-10}$-aryl substituted as defined below, $C_{6-10}$-aroyl, $C_{6-10}$-aroyl substituted as defined below for aryl, dialkylamino or trialkylammonium, (d) $C_{3-10}$-cycloalkyl, (e) $C_{1-4}$-alkyl-$C_{3-6}$-cycloalkyl, (f) $C_{6-10}$-aryl, (g) $C_{6-10}$-aryl substituted by 1-3 halogen atoms, a phenyl group, 1-3 $C_{1-4}$-alkyl group or a chloromethyl, fluoromethyl, trifluoromethyl, carboxy, hydroxy or $C_{1-4}$ alkoxy group; a 5- or 6-membered aromatic heterocyclic ring, containing at least one N, O, or S, $R_3$ is an acyl group of a $C_{1-15}$ hydrocarbon carboxylic or sulfonic acid, or one of the $R_2$ groups, A is a —$CH_2$—$CH_2$ or cis-$CH$=$CH$ group, B is a —$CH_2$—$CH_2$— or trans-$CH$=$CH$— or —$C$≡$C$— group, W is —CHOR— or

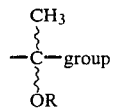

wherein the respective OR groups can be in the alpha- or beta-position,

D and E jointly means a direct bond or

D is straight chain or branched $C_{1-10}$-alkylene or $C_{2-10}$ alkenylene; or $C_{1-10}$-alkylene or $C_{2-10}$ alkenylene each substituted by fluorine, E is oxygen, sulfur, a direct bond, —$C$≡$C$— or —$CR_6$=$CR_7$— wherein $R_6$ is a hydrogen atom or $C_{1-6}$ alkyl and $R_7$ is a hydrogen atom, $C_{1-6}$-alkyl or halogen, $R_4$ is OR, R is H, an acyl group of a $C_{1-15}$ hydrocarbon carboxylic or sulfonic acid, tetrahydropyranyl, tetrahydrofuranyl, alpha-ethoxyethyl, trimethylsilyl, dimethylsilyl, tertbutylsilyl or tribenzylsilyl;

$R_5$ is (a) H, (b) $C_{1-10}$-alkyl, (c) $C_{2-10}$-alkenyl, (d) $C_{1-10}$ alkyl or $C_{2-10}$-alkenyl each substituted by halogen, $C_{6-10}$-aryl or $C_{6-10}$-aryl substituted as defined for $R_2$, (e) $C_{3-10}$-cycloalkyl or $C_{3-10}$-cycloalkyl substituted by $C_{1-4}$-alkyl, (f) $C_{6-10}$-aryl or $C_{6-10}$-aryl substituted as defined for $R_2$, or (g) a 5- or 6-membered aromatic heterocyclic ring containing at least one N, O or S, atom or, when $R_2$ is H, a pharmaceutically acceptable salt thereof with a base.

2. A compound of claim 1 wherein Hal is a fluorine atom.

3. A compound of claim 1 wherein Hal is a chlorine atom.

4. A compound of claim 1 wherein B is trans—$CH$=$CH$—.

5. A compound of claim 1 wherein W is —CHOR—.

6. A compound of claim 1 wherein E is O and $R_5$ is aryl.

7. A compound of claim 1 wherein E is —C≡C— in the 18-position.

8. A compound of claim 1 wherein $DER_5$ is alkylene.

9. A compound of claim 1 wherein $DER_5$ is alkenylene.

10. A compound of claim 1 wherein A is C—C.

11. A compound of claim 1 wherein A is —C≡C—.

12. (2E,13E)-(9R, 11R,15R)-11,15-dihydroxy-9-fluoro-16-phenoxy-17,18,19,20-tetranor-2,13-prostadienoic acid methyl ester;

(2E,13E)-(9R, 11R,15R)-11,15-dihydroxy-9-fluoro-16-phenoxy-17,18,19,20-tetranor-2,13-prostadienoic acid;

(2E,13E)-(9S, 11R,15R)-11,15-dihydroxy-9-fluoro-16-phenoxy-17,18,19,20-tetranor-2,13-prostadienoic acid methyl ester;

(2E,13E)-(9S, 11R,15R)-11,15-dihydroxy-9-floro-16-phenoxy-17,18,19,20-tetranor-2,13-prostadienoic acid;

(2E,13E)-(9R, 11R,15R)-11,15-dihydroxy-16,16-dimethyl-9-fluoro-2,13-prostadienoic acid methyl ester;

(2E,13E)-(9R, 11R,15R)-11,15-dihydroxy-16,16-dimethyl 9-fluoro-2,13-prostadienoic acid;

(2E,13E)-(9R, 11R,15S,16RS)-11,15-dihydroxy-9-fluoro-16-methyl-2,13-prostadienoic acid methyl ester;

(2E,13E)-(9R, 11R,15S,16RS)-11,15-dihydroxy-9-fluoro-16-methyl-2-13-prostadienoic acid;

(2E,13E)-(9E, 11R,15-dihydroxy-16,19-dimethyl-99-fluoro-2,13,18-prostatrienoic acid methyl ester;

(2E,13E)-(9R, 11R,15S,16RS)-11,15-dihydroxy-16,19-dimethyl-9-fluoro-2,13,18-prostatrienoic acid methyl ester;

(2E,13E-(9E, 11R,15RS)-11,15-dihydroxy-9-fluoro-15-methyl-2,13-prostadienoic acid methyl ester;

(2E,13E)-(9R, 11R,15RS(-11,15-dihydroxy-9-fluoro-15-methyl-2,13-prostadienoic acid;

(2E,13E)-(9R, 11R,15S)-11,15-dihydroxy-9-fluoro-2,13-prostadienoic acid methyl ester;

(2E,13E)-(9R, 11R,15S)-11,15-dihydroxy-9-fluoro-2,13-prostadienoic acid;

(2E,13E)-(9R, 11R,15R)-9-chloro-11-,15-dihydroxy-16-phenoxy-17,18,19,20-tetranor-2,13-prostadienoic acid methyl ester;

(2E,13E)-(9R, 11R,15R)-9-chloro-11,15-dihydroxy-16-phenoxy-17,18,19,20-tetranor-2,13-prostadienoic acid;

(2E,13E)-(9S, 11R,15R)-9-chloro-11,15-dihydroxy-16-phenoxy-17,18,19,20-tetranor-2,13-prostadienoic acid methyl ester;

(2E,13E)-(9S, 11R,15R)-9-chloro-11,15-dihydroxy-16-phenoxy-17,18,19,20-tetranor-2,13-prostadienoic acid;

(2E,13E)-(9R, 11R,15R)-9-chloro-11,15-dihydroxy-16,16-dimethyl-2,13-prostadienoic acid methyl (2E,13E)-(9R, 11R,15R)-9-chloro-11,15-dihydroxy-16,16-dimethyl-2,13-prostadienoic acid;

(2E,13E)-(9R, 11R,15S,16RS)-9-chloro-11,15-dihydroxy-16-methyl-2,13-prostadienoic acid;

(2E,13E)-(9R, 11R,15S,16RS)-9-chloro-11,15-dihydroxy-16-methyl-2,13-prostadienoic acid;

(2E,13E)-(R, 11R,15RS)-9-chloro-11,15-dihydroxy-15-methyl-2,13-prostadienoic acid methyl ester;

(2E,13E)-(9R, 11R,15RS)-9-chloro-11,15-dihydroxy-15-methyl-2,13-prostadienoic acid;

(2E,13E)-(9R, 11R,15S)-9-chloro-11,15-dihydroxy-2,13-prostadienoic acid methyl ester;

(2E,13E)-(-R, 11R,15S)-9-chloro-11,15-dihydroxy-2,13-prostadienoic acid;

(2E,5Z,13E)-(9R, 11R,15R)-9-chloro-11,15-dihydroxy-16,16-dimethyl-2,5,13-prostatrienoic acid methyl ester;

(2E,5Z,13E)-(9R, 11R,15R)-9-chloro-11,15-dihydroxy-16,16-dimethyl-2,5,13-prostatrienoic acid;

(2E,5Z,13E)-(9R, 11R,15R)11,15-dihydroxy-16,16-dimethyl-9-fluoro-2,5,13-prostatrienoic acid methyl ester;

(2E,5Z,13E)-9R, 11R,15R)-11,15-dihydroxy-16,16-dimethyl-9-fluoro-2,5,13-prostatrienoic acid;

(2E,13E)-(9R, 11R,15R)-11,15-dihydroxy-9-fluoro-16-phenoxy- 17,18,19,20-tetranor-2,13-prostadienoic acid methylsulfonamide;

(2E,13E)-(9r, 11R,15R)-9-chloro-11,15-dihydroxy-16,16-dimethyl-2,13-prostadienoic acid n-acetylamide; or (2E,13E)-(9R, 11R,15R)-11,15-dihydroxy-9-fluoro-16-phenoxy-17,18,19,20-tetranor-2,13-prostadienoic acid tris9hdroxymethyl)aminomethane salt, each a compound of claim 1.

13. A pharmaceutical composition containing a uterotropica lly effective amount of a compound of claim 1 and a pharmaceutica lly acceptable carrier.

14. A pharmaceutical composition containing a luteolytica lly effective amount of a compound of claim 1 and a pharmaceutica lly acceptable carrier.

15. A method of triggering a uterus contraction in a patient in need of such treatment comprising administering thereto an amount of a compound of claim 1 sufficient to trigger a uterus contraction.

16. A method of inducing luteolysis in a patient in need of such treatment comprising administering thereto a luteolytica lly effective amount of a compound of claim 1.

17. A method of triggering an abortion in a patient in need of such treatment comprising administering therto an abortion-triggering amount of a compound of claim 1.

* * * * *